US010182872B2

(12) United States Patent
Chang et al.

(10) Patent No.: US 10,182,872 B2
(45) Date of Patent: Jan. 22, 2019

(54) POSITIONING MARK APPARATUS OF A SURGERY NAVIGATION SYSTEM AND IMPLEMENTATION INSTRUMENT THEREOF

(71) Applicant: METAL INDUSTRIES RESEARCH & DEVELOPMENT CENTRE, Kaohsiung (TW)

(72) Inventors: Chin-Yu Chang, Taichung (TW); Bing-Feng Huang, Kaohsiung (TW); Yen-Ting Liu, Kaohsiung (TW); Chih-Lung Lin, Kaohsiung (TW)

(73) Assignee: Metal Industries Research and Develoment Centre, Kaohsiung (TW)

( * ) Notice: Subject to any disclaimer, the term of this patent is extended or adjusted under 35 U.S.C. 154(b) by 282 days.

(21) Appl. No.: 15/147,900

(22) Filed: May 5, 2016

(65) Prior Publication Data

US 2017/0319280 A1    Nov. 9, 2017

(51) Int. Cl.
*A61B 34/20*    (2016.01)
*A61B 17/88*    (2006.01)
*A61B 90/00*    (2016.01)

(52) U.S. Cl.
CPC .......... *A61B 34/20* (2016.02); *A61B 17/8875* (2013.01); *A61B 90/39* (2016.02); *A61B 2034/2055* (2016.02); *A61B 2034/2068* (2016.02); *A61B 2034/2072* (2016.02); *A61B 2090/3916* (2016.02); *A61B 2090/3975* (2016.02); *A61B 2090/3983* (2016.02); *A61B 2562/166* (2013.01)

(58) Field of Classification Search
CPC ............ A61B 34/20; A61B 2034/2055; A61B 2034/2068; A61B 2034/2072; A61B 2090/3916; A61B 2090/3983; A61B 2562/166
See application file for complete search history.

(56) References Cited

U.S. PATENT DOCUMENTS

| | | | |
|---|---|---|---|
| 6,203,543 | B1 | 3/2001 | Glossop |
| 6,719,757 | B2 | 4/2004 | Neubauer et al. |
| 6,893,447 | B2 | 5/2005 | Dominguez et al. |

(Continued)

*Primary Examiner* — Larry E Waggle, Jr.
(74) *Attorney, Agent, or Firm* — Juan Carlos A. Marquez; Marquez IP Law Office, PLLC (57) ABSTRACT

A positioning mark apparatus of a surgery navigation system and an implementation instrument thereof are disclosed. The positioning mark apparatus includes a positioning base and a frequency modulated radio frequency positioning module. One end of the positioning base is a lock portion having a screw structure, another end is a head having a joint structure, and a free end of the head has a fitting structure. The frequency modulated radio frequency positioning module has a sleeving structure that cooperates with the head structure and buckles with the joint structure. The frequency modulated radio frequency positioning module includes an antenna unit, a printed circuit board unit electrically connected to the antenna unit, and an electronic component battery unit supplying power to the printed circuit board unit. The frequency modulated radio frequency positioning module may transmit, according to a received frequency modulated signal, a feedback signal including a radio frequency signal to the external.

9 Claims, 8 Drawing Sheets

(56) References Cited

U.S. PATENT DOCUMENTS 8,057,407 B2 * 11/2011 Martinelli .............. A61B 34/20
600/407
8,911,448 B2 * 12/2014 Stein ....................... A61F 2/442
606/102

* cited by examiner

POSITIONING MARK APPARATUS OF A SURGERY NAVIGATION SYSTEM AND IMPLEMENTATION INSTRUMENT THEREOF

BACKGROUND OF THE INVENTION

Field of Invention

The present invention relates to a positioning mark apparatus of a surgery navigation system and an implementation instrument thereof, and in particular, to a positioning mark apparatus that is applied in a surgery navigation system, that is disposed at an operation position, and that provides frequency modulated radio frequency dynamic reference coordinates and an implementation instrument thereof.

Related Art

Currently, in a surgery navigation process, besides that an instrument needs to be installed with a positioning component, a human body also needs to be installed with an apparatus calibration object to acquire a reference framework, to further aid a surgical instrument in guidance. Therefore, a manner in which the calibration object and human tissues are combined needs certain convenience and stability, to satisfy an environmental requirement of surgery navigation. Currently, in a mainstream infrared space tracking and positioning system, by using Preoperative CT scans and in combination with a dynamic reference frame (DRF) and a registration step that are installed on a surgical instrument and a vertebra, positioning and tracking of a surgical instrument and human tissues are achieved. Currently, the positioning of the vertebra is mainly completed by using a dynamic reference framework mark unit fastened to a spinous process. However, disadvantages are: (1) construction of the dynamic reference framework needs to be after the computer CT scans, resulting in a phenomenon that space relative positions of the human vertebrae are different in taking of brain CT scans and an actual operation; (2) a dynamic reference framework marker is easily shielded by the body of a patient and another surgical instrument in an operation process, causing a phenomenon that the dynamic reference framework marker cannot be positioned; (3) movement of the calibration object caused by a surgeon and another instrument easily causes a phenomenon of a positioning error; (4) the calibration object needs to be higher than the human body surface and has a large volume, which affects the surgeon; (5) the calibration object is designed to be of a structure of clamping a spinous process, and the structure is not stable enough.

A U.S. Pat. No. 6,719,757 B2 discloses an apparatus for setting a surgery guidance unit in a human body. The apparatus is used in a minimally invasive surgery and enables a surgical unit (a positioning mark for guidance) to be firmly connected to a patient body, and in particular, to a bone or a joint. However, the apparatus may also be applied to various open surgeries according to the present invention. There is the possibility that a positioning component is moved only when a rotor and a rod in the technology crashes with a surgeon or another object in an operation.

A U.S. Pat. No. 6,893,447 B2 discloses a surgical reference framework supporting apparatus and an application method. The surgical reference framework supporting apparatus is used in a brain minimally invasive surgery, and connects a surgical reference positioning unit to a head of a patient, and includes a support bracket, a hollow rod, a base, an anchor pipe, and a percutaneous needle. In the technology, a component easily moves or the lesion is easily damaged only when a collision occurs when the percutaneous needle architecture is used to fasten surgical apparatuses.

A U.S. Pat. No. 6,203,543 B1 discloses an apparatus that has an adjustable function and may fasten an object to a bone. The apparatus is used in an orthopedic surgery, connects a surgical reference positioning unit to a bone of a patient, and includes a rotation limiting unit, and an axial support unit. In the technology, cases of collision and movement occurring in an operation increase only when a structure connected to a positioning unit is located at the axial side and the volume is difficult to contract.

SUMMARY OF THE INVENTION

An objective of the present invention is to provide a positioning mark apparatus of a surgery navigation system and an implementation instrument. The positioning mark apparatus of the surgery navigation system includes a positioning base and a frequency modulated radio frequency positioning module connected to the positioning base; and can effectively improve efficiency and accuracy of spine positioning performed by a surgeon, avoid a shielding phenomenon occurring in a current existing infrared guidance technology, and achieve a goal that each of multiple vertebrae has an independent reference positioning point by means of a miniaturized volume and simultaneous installment of the multiple vertebrae in a spine navigation surgery process, thereby further greatly improving safety and reliability of the intelligent guidance surgery.

To achieve the foregoing objective, a structure of a positioning mark apparatus according to the present invention includes a positioning base and a frequency modulated radio frequency positioning module. Two ends of the positioning base are a lock portion and a head. The lock portion has a screw structure, a free end of the head has a fitting structure, and the head has a joint structure. The frequency modulated radio frequency positioning module has a sleeving structure that cooperates with the head structure and buckles with the joint structure, so as to make the frequency modulated radio frequency positioning module installed on the head of the positioning base. The frequency modulated radio frequency positioning module includes an antenna unit that receives a frequency modulated signal and sends a feedback signal, a printed circuit board unit electrically connected to the antenna unit, and an electronic component battery unit supplying power to the printed circuit board unit. The frequency modulated radio frequency positioning module may transmit a feedback signal to the external according to a received frequency modulated signal.

To achieve the foregoing objective, the implementation instrument according to the present invention includes a handle and a pole body connected to the handle, where a head end of the pole body has a driving portion that cooperates with and that fits the end face shape of the fitting structure.

As described above, features of the present invention include at least: (1) in the present invention, a wireless positioning technology is used and therefore there is no shielding phenomenon occurring in use of an existing infrared guidance technology; and there is no a phenomenon during an operation that a navigation function fails because of shielding of a surgeon and another object; (2) the wireless positioning technology used in the present invention can make a unit volume of a frequency modulated radio frequency positioning module, as a DRF, in a positioning mark apparatus contract within 5 mm×10 mm. In a manner of mutual installment of miniature bone nails fastened to a spinous process by using an execution instrument, stability of attachment to a vertebra increases. An injection opening is controlled within 5 mm, so that an uncomfortable feeling of a patient is greatly relieved. A volume of a part higher than the body surface can be greatly reduced. According to the operation, computer CT scans may be taken after installment of a dynamic reference framework unit, which can effectively reduce errors in vertebra positions of an image of the computer CT scans and a practical operation; (3) according to the present invention, multiple positioning mark apparatuses may be installed on multiple vertebrae, so that each vertebra has an independent reference positioning point, which can break the intuitive limit during positioning, and effectively improve accuracy of positioning; (4) during an operation, image coordinate registration may be fast performed. During a system setting operation, a set registration point already installed on the dynamic reference framework may be selected, so that a vertebra coordinate registration may be performed fast, thereby effectively improving positioning accuracy and reducing setting time.

BRIEF DESCRIPTION OF THE DRAWINGS

The disclosure will become more fully understood from the detailed description given herein below for illustration only, and thus are not limitative of the disclosure, and wherein.

DETAILED DESCRIPTION OF THE INVENTION

The following describes embodiments of this specification in detail with reference to the accompanying drawings.

All of the accompanying drawings are simplified into schematic diagrams and merely describe a basic structure of this specification in a schematic manner. Therefore, the accompanying drawings merely show components related to this specification, and the shown components are not drawn according to quantities, shapes, and size proportions of the components when the components are implemented. When the components are actually implemented, specifications and sizes of the components actually are a selective design, and the layout and shape of the components may be more complicated.

As shown in FIG. 1 to FIG. 4 and FIG. 5, in this embodiment, because a positioning mark apparatus 10 is applied to the surgery field, a material for making the positioning mark apparatus 10 applied to a surgery navigation system has anti-erosion, anti-radiation, insulation, and biocompatibility features. A structure of the positioning mark apparatus 10 of the surgery navigation system includes a positioning base 11 and a frequency modulated radio frequency positioning module 12. The positioning base 11 includes two ends: a tail end of the positioning base 11 is a lock portion 111, and a head end is a head 112. The frequency modulated radio frequency positioning module 12 is installed in the head 112 of the positioning base 11, and the frequency modulated radio frequency positioning module 12 includes an antenna unit 122, a printed circuit board (PCB) unit 123, and an electronic component battery unit 124. The printed circuit board unit 123 is electrically connected to the antenna unit 122. The printed circuit board unit 123 herein may include a necessary electronic component 1231 disposed on the printed circuit board unit 123. The electronic component battery unit 124 supplies power to the printed circuit board unit 123. The antenna unit 122 may receive a frequency modulated signal R from the external and transmit a feedback signal 20 including a radio frequency signal. Preferably, generally, a frequency that may trigger the feedback signal 20 is a frequency same with a frequency that may be transmitted by the antenna unit 122, that is, frequencies of the feedback signal 20 and the frequency modulated signal R are the same, for example, application of a radio frequency identification (RFID) technology.

Specifically, the positioning base 11 may be fastened to a patient in a typical screw lock manner (however, the present invention is not limited to the manner, and any manner in which an implementation instrument on the patient may be firmly combined is available). For example, the lock portion 111 has a screw structure. A free end of the head 112 has a fitting structure 1121 (an end face of the fitting structure 1121 may have a shape of a single groove or a square groove), and the fitting structure 1121 may be combined with the following implementation instrument 30 (which is described in FIG. 7 to FIG. 11 below), which facilitates to transmit a driving torque force of the implementation instrument 30 to the positioning base 11, so as to install the screw lock (for example, a spinous process A that is installed on a patient in a spine surgery).

In addition, the head 112 has a joint structure 1122 (the joint structure 1122 in this embodiment is a concave base 11221 disposed on a side face of the head 112 and an assembly hole 11222 disposed inside the concave base 11221), so that after being installed to a desirable position, the positioning base 11 and the frequency modulated radio frequency positioning module 1122 are connected. Correspondingly, the frequency modulated radio frequency positioning module 12 has a sleeving structure 121 (in this embodiment, the sleeving structure 121 is a groove 1211 and positioning structures 1212 that correspond to the assembly hole 11222 and an inner wall of grooves 1122) that cooperates with a cylindrical structure of the head 112 and that buckles with the joint structure 1122, so as to make the frequency modulated radio frequency positioning module 12 installed on the head 112 of the positioning base 11.

Figure 1:
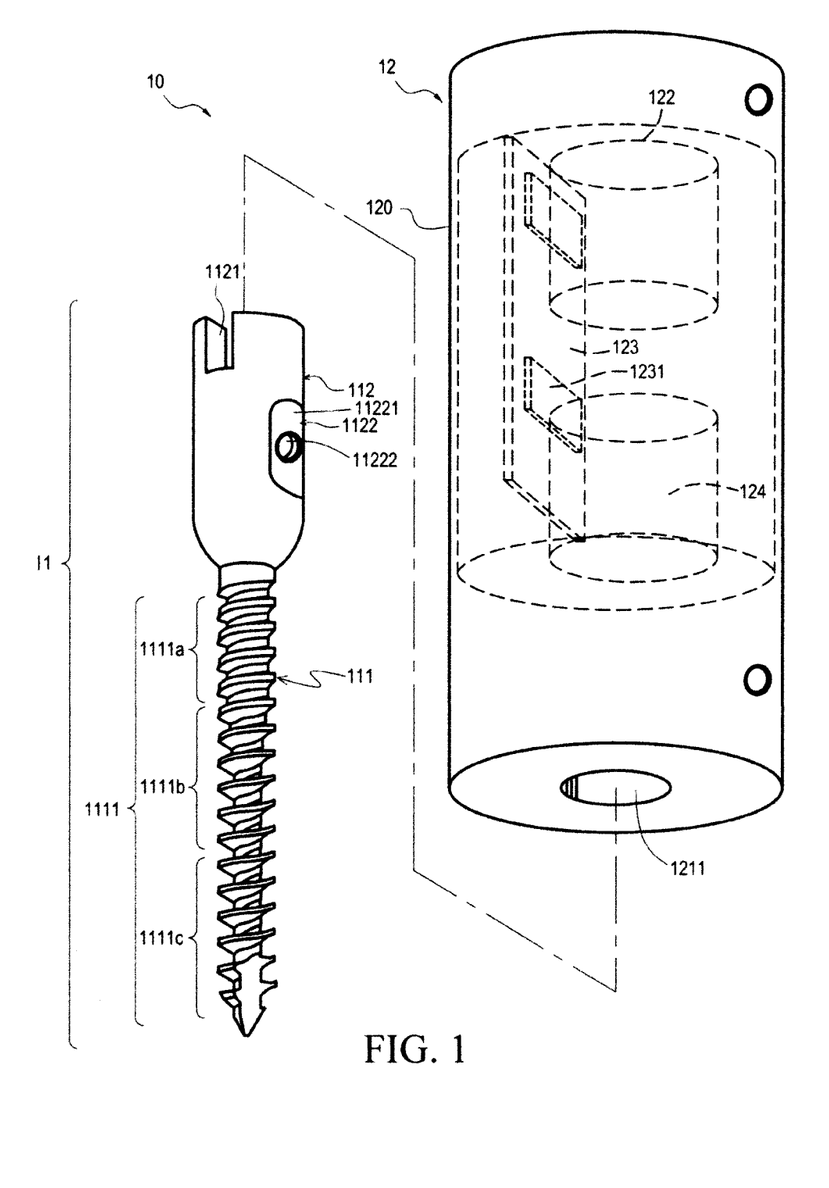
FIG. 1 is a block exploded view of an embodiment of a positioning mark apparatus of a surgery navigation system according to the present invention.

In an embodiment, the lock portion 111 of the foregoing positioning base 11 may be a self-lock screw, so as to directly lock an installment position firmly during installment. In addition, in an embodiment, the lock portion 111 of the positioning base 11 may be a spinous process bone nail, for example, a self-lock cortical/cancellous bone nail having a progressive thread (as shown in FIG. 1) sequentially formed of a cancellous thread 1111*a*, a transitional thread 1111*b*, and a cortical thread 1111*c*. That is, the spinous process bone nail may be autonomously fastened to a cortical layer of a spine bone of the patient, thereby achieving a good fastening effect.

Figure 2A:
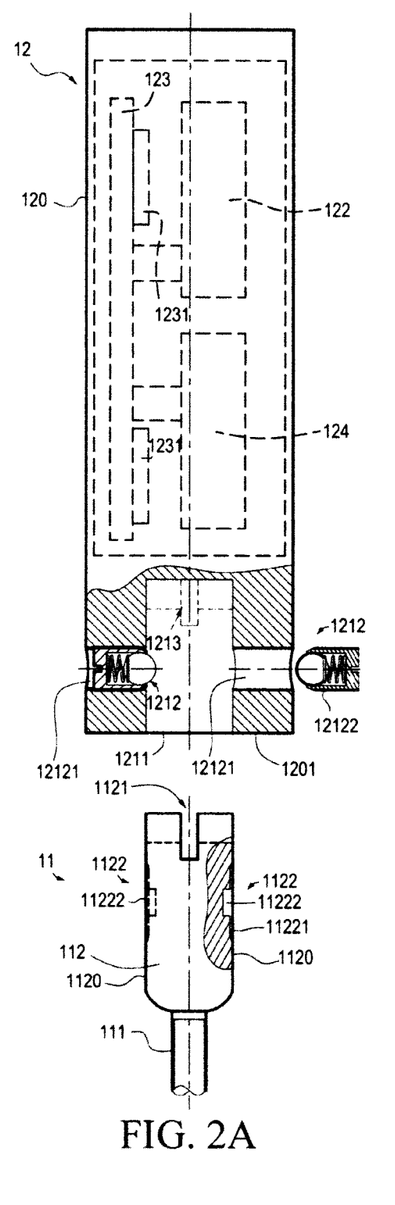
FIG. 2 is a front-view exploded view of an embodiment of a positioning mark apparatus of a surgery navigation system according to the present invention.
Figure 2B:
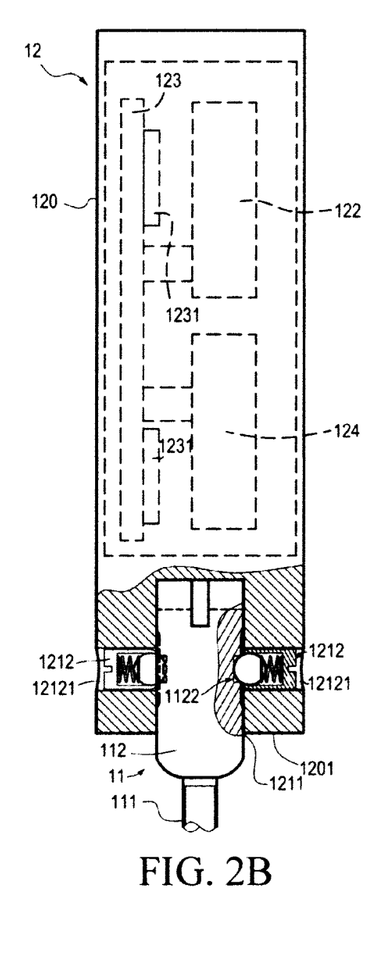
FIG. 2B is a front-view combination diagram of FIG. 2A.
Figure 3:
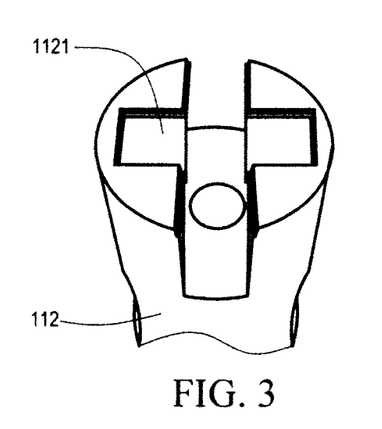
FIG. 3 is a block diagram of an embodiment of a fitting structure of a positioning base of a positioning mark apparatus of a surgery navigation system according to the present invention.
Figure 4:
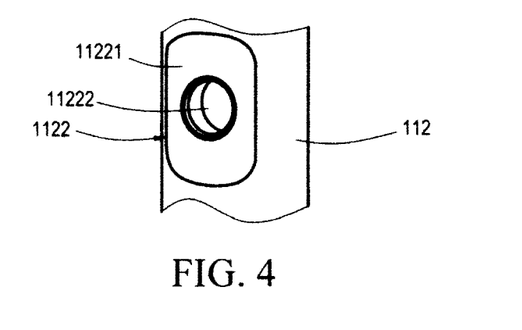
FIG. 4 is a block diagram of an embodiment of a joint structure of a positioning base of a positioning mark apparatus of a surgery navigation system according to the present invention.

As shown in FIG. 2A and FIG. 2B, in this embodiment, the joint structure 1122 is disposed on a side face 1120, which is perpendicular to the free end, of the head 112 and includes a concave base 11221 and at least one assembly hole 11222 or a pair of assembly holes 11222 that are circularly disposed and evenly distributed on a radial surface of the side face 1120. The sleeving structure 121 is disposed on a surface 1201, which faces the head 112, of the frequency modulated radio frequency positioning module 12 and includes a groove 1211 corresponding to a diameter size of the head 112. A position of an inner wall surface of the groove 1211 corresponding to the assembly hole 11222, which sleeves the groove 1211, of the head 112 is provided with a positioning structure 1212, so that after covering the head 112 of the positioning base 12, the groove 1211 may perform mutual installment and maintain a lock state by using interaction between the positioning structure and the assembly hole. Certainly, on practical designing of sleeving of a column-shaped or a hole-shaped structure, as shown in FIG. 2A and FIG. 2B, the positioning structure 1212 may be a positioning ball component 12122 and cooperates with a screw hole 12121 disposed in a direction perpendicular to the inner wall surface of the groove 1211, so that the positioning ball component 12122 enters the screw hole 12121 like a screw. A surface of the positioning ball component 12122 is higher than the inner wall surface of the groove 1211, so as to correspondingly have functions of an elastically positioning combination and removing a combination by cooperating with the assembly hole 11222.

Further, as shown in FIG. 2A and FIG. 2B, a bottom end face of the groove 1211 includes a fitting shape structure 1213 that cooperates with an end face shape of the fitting structure 1121 for mutually fitting, so that when the positioning structure 1212 buckles with the assembly hole 11222, the fitting shape structure 1213 is simultaneously joint with the fitting structure 1121, so as to solidify connection stability of the joint structure 1122 and the sleeving structure 121, and further improve a positioning effect of the frequency modulated radio frequency positioning module 12 on the positioning base 11.

In an embodiment, the frequency modulated radio frequency positioning module 12 further includes a package housing 120 that packages the antenna unit 122, the printed circuit board unit 123, and the electronic component battery unit 124 (a specific implementation manner is to package, by using a package material, the antenna unit 122, the printed circuit board unit 123, and the electronic component battery unit 124 disposed within inner space of the package housing 120), and a surface of the package housing 120 forms the sleeving structure 121 (as shown in FIG. 1, FIG. 2A, and FIG. 2B).

Figure 5:
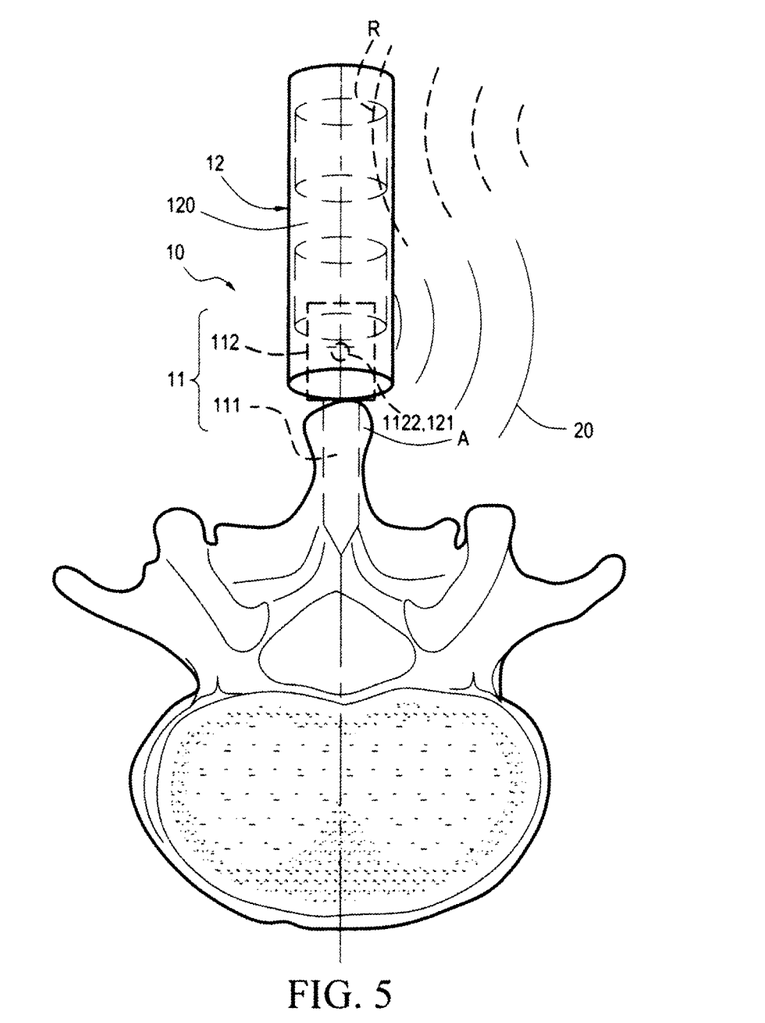
FIG. 5 is a schematic dynamic diagram of an embodiment in which a positioning mark apparatus of a surgery navigation system according to the present invention is installed on a spinous process.

Further, as shown in FIG. 5, in an embodiment, the feedback signal 20 includes a frequency signal 21 of the frequency modulated radio frequency positioning module 12, so that a surgery navigation system (which is not shown in the figure) identifies coordinate information of the positioning mark apparatus 10. The feedback signal 20 may further include an identifier signal 22 of a hardware device of the frequency modulated radio frequency positioning module 12, so that an external system (for example, the surgery navigation system) identifies hardware information of the positioning mark apparatus 10. With reference to the frequency signal 21 transmitted by same hardware described above, the surgery navigation system may acquire any information of the positioning mark apparatus 10 related to the coordinate position and make use of the information.

Figure 6:
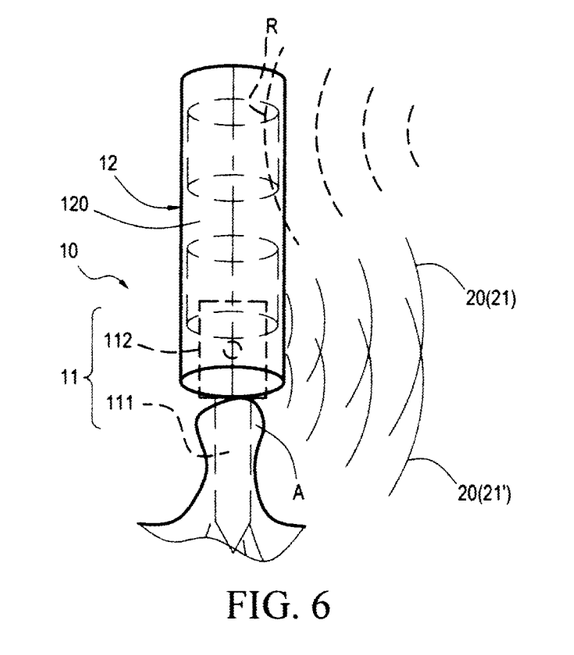
FIG. 6 is a schematic dynamic diagram showing that an embodiment of two antennas of a positioning mark apparatus of a surgery navigation system according to the present invention is installed on a spinous process.
Figure 7:
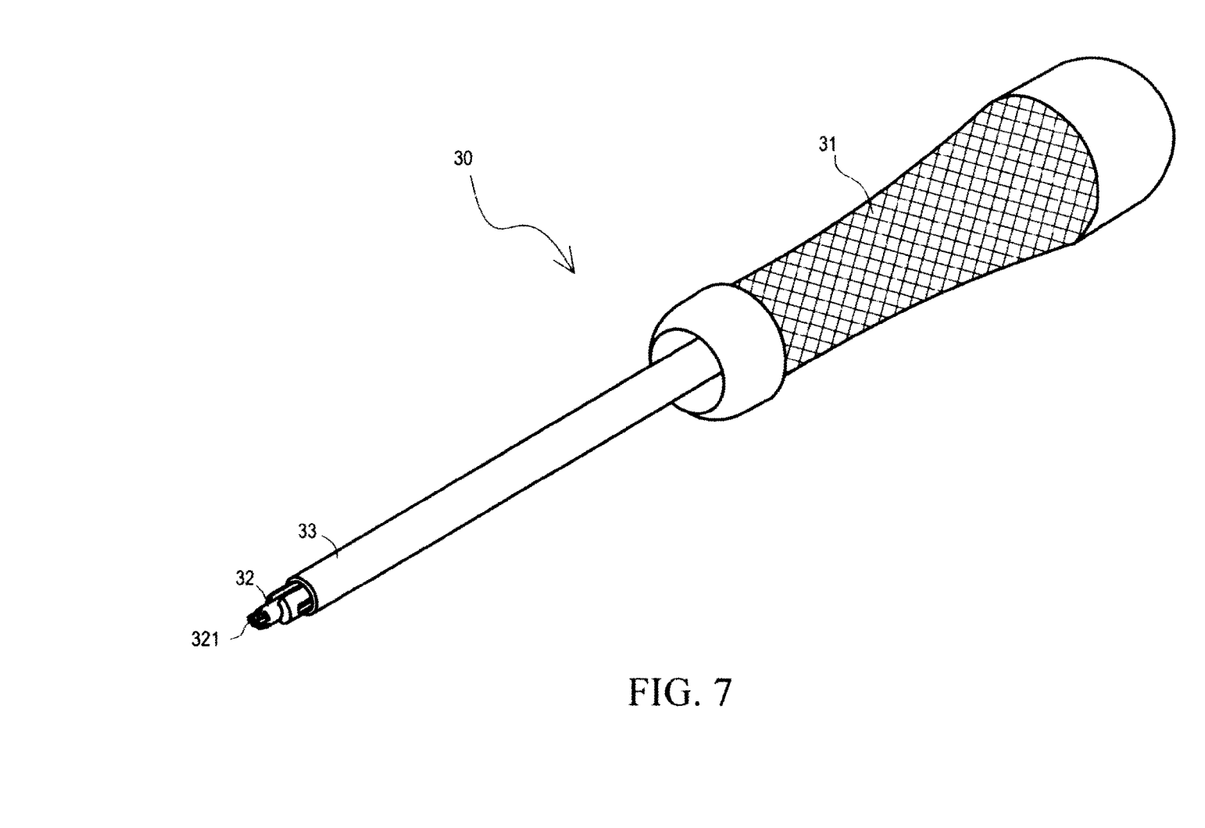
FIG. 7 is a block diagram of an embodiment of an implementation instrument of a positioning base of a positioning mark apparatus of a surgery navigation system according to the present invention.
Figure 8:
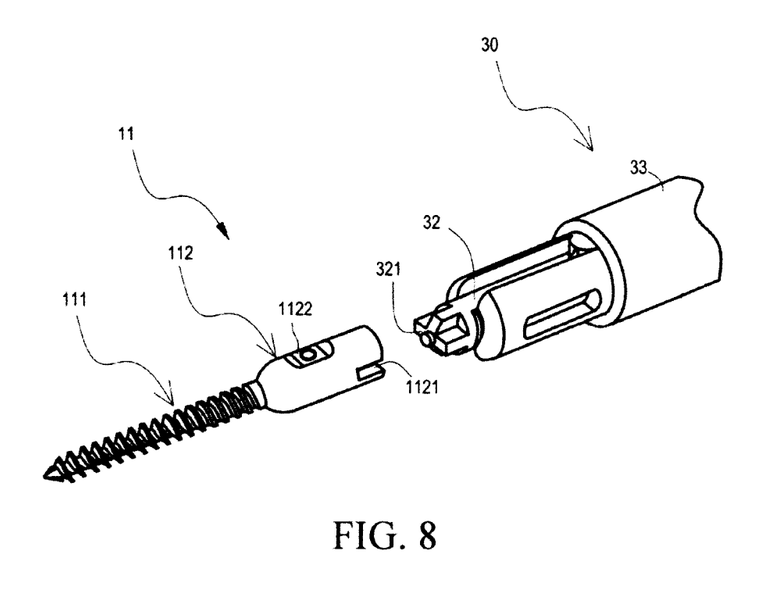
FIG. 8 to FIG. 11 are structural process block diagrams of a process in which a positioning base of a positioning mark apparatus of a surgery navigation system and an implementation instrument are combined according to the present invention.
Figure 9:
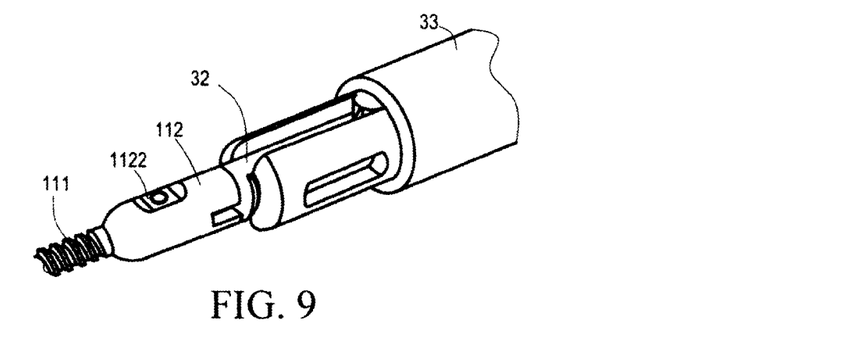
Figure 10:
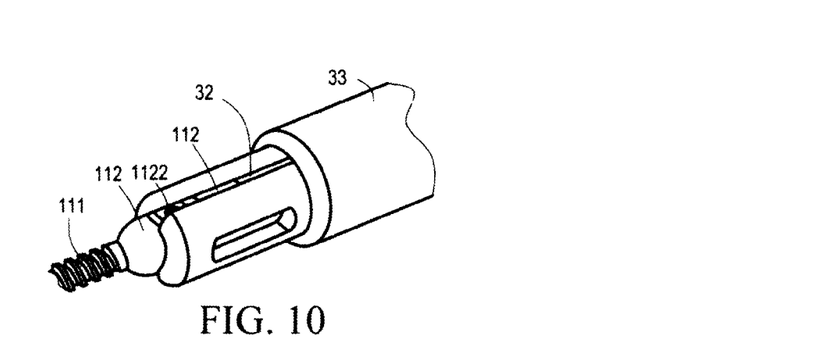
Figure 11:
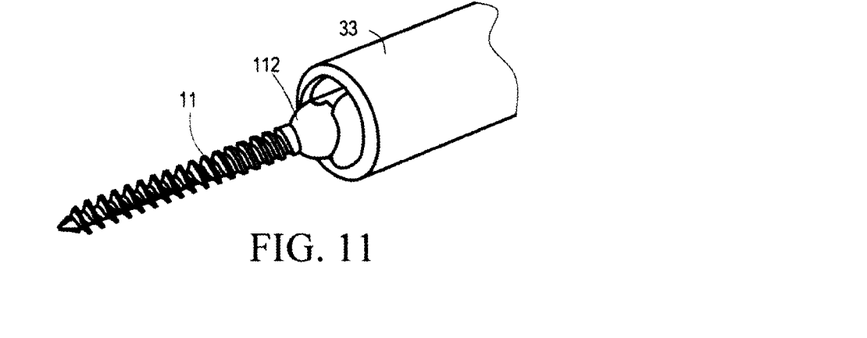

As shown in FIG. 6, in this embodiment, an antenna unit 122 has two antennas. The feedback signal 20' includes two frequency signals (21, 21') that are separately transmitted by the two antennas, so that the surgery navigation system calculates coordinate information of the positioning mark apparatus 10 more accurately according to the two frequency signals (21, 21') in different angles.

Further, as shown in FIG. 7 to FIG. 11, the present invention further includes an implementation instrument 30 of a positioning base 11 (that is, an execution apparatus that puts the positioning base 11 into a patient). The implementation instrument 30 has a handle 31, and a pole body 32 connected to the handle 31. A head end of the pole body 32 has a driving portion 321 cooperating with a shape of the head end 112 (or the fitting structure 1121), so as to buckle with the fitting structure 1121 and be in an axial connection state.

Further, an external side face of the pole body 32 further includes a sleeve tube portion 33 that may be in a coverage state when the sleeve tube portion 33 is corresponding to the head 112 of the positioning base 11 and may be in an uncovered state when the sleeve tube portion 33 and the head 112 of the positioning base 11 are staggered, so that after the driving portion 321 of the pole body 32 and the fitting structure 1121 of the positioning base 11 are combined in the uncovered state, the sleeve tube portion 33 is further switched to be in the coverage state. In this way, the fitting structure 1121 of the positioning base 11 and the driving portion 321 of the pole body 32 are in a clamping state because of coverage of the sleeve tube portion 33 (a practical operation may be that a position, which corresponds to the joint structure 1122, of the sleeve tube portion 33 is provided with such as a corresponding magnetic component or a positioning ball component, so as to generate a combination effect by interacting with the joint structure 1122), so as to perform an installment operation on a spinous process A.

According to the foregoing structure, when a surgery navigation system for a spine surgery is used in the present invention, the positioning mark apparatus 10 may use the foregoing implementation instrument 30, to make of lock portions 111 of one or more positioning bases 11 are separately screw-locked to a spinous process A of multiple vertebrae of a patient, and to make the head 112 of the positioning base 11 expose to the external. Then frequency modulated radio frequency positioning modules 12 corresponding to a quantity of the positioning bases 11 are separately combined with the heads 112 (to make the sleeving structure 121 combine the joint structure 1122), to form a dynamic reference frame (DRF) of the surgery navigation system, that is, when the surgery navigation system sends a positioning query frequency modulated signal, antenna units 122 of the frequency modulated radio frequency positioning modules 12 may obtain a coordinate position of an installed spinous process A through calculation according to a feedback signal 20 transmitted by each frequency modulated radio frequency positioning module 12, to further provide related positioning information, which helps and guides use of a surgical instrument in an operation process.

Implementation manners or embodiments of the technical solutions used in the present invention are not intended to limit the patent implementation scope of this application. Any equivalent changes or modifications made in accordance with the claims of the present invention or within the scope of the present invention shall fall within the protection scope of the present invention.

What is claimed is:

1. A positioning mark apparatus of a surgery navigation system, comprising:
    a positioning base, wherein one end of the positioning base is a lock portion, another end is a head, and a free end of the head has a fitting structure; and
    a frequency modulated radio frequency positioning module, which is installed in the head of the positioning base and comprises an antenna unit, a printed circuit board unit electrically connected to the antenna unit, and an electronic component battery unit supplying power to the printed circuit board unit, wherein the frequency modulated radio frequency positioning module may transmit, according to a received frequency modulated signal, a feedback signal comprising a radio frequency signal outputted externally,
    wherein the frequency modulated radio frequency positioning module further comprises a package housing that packages the antenna unit, the printed circuit board unit, and the electronic component battery unit, and a surface of the package housing forms a sleeving structure.

2. The positioning mark apparatus of a surgery navigation system according to claim 1, wherein the head has a joint structure, the sleeving structure cooperates with the head and buckles with the joint structure, the joint structure is disposed on a side face, which is perpendicular to the free end, of the head and comprises at least one assembly hole, the sleeving structure is disposed on a surface, which faces the head, of the frequency modulated radio frequency positioning module and comprises a groove corresponding to a diameter of the head, and a position of an inner wall surface of the groove corresponding to the assembly hole, which sleeves the groove, of the head is provided with a positioning structure, so that after covering the head of the positioning base, the groove may perform mutual installment and maintain a lock state by using interaction between the positioning structure and the assembly hole.

3. The positioning mark apparatus of a surgery navigation system according to claim 2, wherein a bottom end face of the groove comprises a fitting shape structure that cooperates with an end face shape of the fitting structure for mutually fitting, so that when the positioning structure buckles with the assembly hole, the fitting shape structure is simultaneously jointed with the fitting structure.

4. The positioning mark apparatus of a surgery navigation system according to claim 1, wherein the positioning base is a self-lock cortical/cancellous bone nail with a progressive thread.

5. The positioning mark apparatus of a surgery navigation system according to claim 1, wherein the feedback signal comprises a frequency signal of the frequency modulated radio frequency positioning module.

6. The positioning mark apparatus of a surgery navigation system according to claim 1, wherein the feedback signal comprises an identifier signal of the frequency modulated radio frequency positioning module.

7. The positioning mark apparatus of a surgery navigation system according to claim 1, wherein the antenna unit has two antennas, and the feedback signal comprises two frequency signals transmitted by the two antennas.

8. An implementation instrument of a positioning mark apparatus of a surgery navigation system, comprising:
    a handle; and
    a pole body connected to the handle, wherein a head of the pole body has a driving portion that cooperates with and that fits an end face shape of the head of the positioning mark apparatus according to claim 1.

9. The implementation instrument of a positioning mark apparatus of a surgery navigation system according to claim 8, wherein an outer side face of the pole body further comprises a sleeve tube portion that may cover and uncover the head of the positioning base, so as to make a fitting structure of the positioning base and a driving portion of the pole body in a clamping state when the sleeve tube portion covers the head of the positioning base.

* * * * *